US011305042B2

(12) United States Patent
Glaser

(10) Patent No.: US 11,305,042 B2
(45) Date of Patent: Apr. 19, 2022

(54) DEVICE AND METHOD FOR PREPARING DIALYSIS FLUID AND DIALYSIS DEVICE

(71) Applicant: FRESENIUS MEDICAL CARE DEUTSCHLAND GMBH, Bad Homburg (DE)

(72) Inventor: Benedict Glaser, Schweinfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 521 days.

(21) Appl. No.: 16/325,190

(22) PCT Filed: Aug. 14, 2017

(86) PCT No.: PCT/EP2017/070635
§ 371 (c)(1),
(2) Date: Feb. 13, 2019

(87) PCT Pub. No.: WO2018/036859
PCT Pub. Date: Mar. 1, 2018

(65) Prior Publication Data
US 2019/0167880 A1 Jun. 6, 2019

(30) Foreign Application Priority Data

Aug. 20, 2016 (DE) ...................... 10 2016 010 222.5

(51) Int. Cl.
*A61M 1/16* (2006.01)
*A61M 1/26* (2006.01)
(52) U.S. Cl.
CPC ........ *A61M 1/1639* (2014.02); *A61M 1/1603* (2014.02); *A61M 1/168* (2013.01);
(Continued)

(58) Field of Classification Search
CPC .............. A61M 1/1603; A61M 1/1635; A61M 1/1639; A61M 1/1656; A61M 1/168; A61M 1/267; A61M 2205/3337
See application file for complete search history.

(56) References Cited

U.S. PATENT DOCUMENTS 4,267,040 A   5/1981   Schal
4,618,343 A  10/1986   Polaschegg
(Continued)

FOREIGN PATENT DOCUMENTS

DE   3333362 A1    4/1985
DE  19702213 A1    7/1998
(Continued)

OTHER PUBLICATIONS

International Preliminary Report on Patentability issued in corresponding International Patent Application No. PCT/EP2017/070635 dated Feb. 26, 2019 (9 pages).
International Search Report issued in corresponding International Patent Application No. PCT/EP2017/070635 (with English translation) dated Nov. 14, 2017 (11 pages).

*Primary Examiner* — Dirk R Bass
(74) *Attorney, Agent, or Firm* — Kilyk & Bowersox, P.L.L.C.

(57) ABSTRACT

The invention relates to an apparatus and to a method for supplying dialysate. The invention also relates to a dialysis apparatus comprising an apparatus for supplying dialysate. The apparatus for supplying dialysate has a balancing device 8, which comprises at least one balancing chamber 9, 10 for balancing fresh and used dialysate, and a metering device 28 for filling the at least one balancing chamber with permeate and concentrates in a specified mixing ratio for producing dialysate. The metering device 28 is designed such that specified volumes of concentrates are conveyed into the at least one balancing chamber 9, 10 in successive working cycles. Given that the specified volumes of concentrates are not added simultaneously, the concentrates can be conveyed (Continued)

using just one single metering pump. This is advantageous in that the metering pump is a relatively expensive component of the mixer circuit. In practice, the design is simpler and compact and the maintenance costs are reduced.

14 Claims, 2 Drawing Sheets

(52) U.S. Cl.
CPC ........ *A61M 1/1635* (2014.02); *A61M 1/1656* (2013.01); *A61M 1/267* (2014.02); *A61M 2205/3337* (2013.01)

(56) References Cited

U.S. PATENT DOCUMENTS

| | | | |
|---|---|---|---|
| 8,182,691 | B2 | 5/2012 | Stahl |
| 2005/0011833 | A1* | 1/2005 | Stahl .................. A61M 1/1613 210/646 |
| 2008/0202591 | A1 | 8/2008 | Grant et al. |
| 2016/0000990 | A1 | 1/2016 | Ritter |

FOREIGN PATENT DOCUMENTS

| | | |
|---|---|---|
| DE | 102014109369 A1 | 1/2016 |
| EP | 1491222 A1 | 12/2004 |
| WO | 0232476 A2 | 4/2002 |
| WO | 2005118485 A1 | 12/2005 |

* cited by examiner

DEVICE AND METHOD FOR PREPARING DIALYSIS FLUID AND DIALYSIS DEVICE

This application is a National Stage Application of PCT/EP2017/070635, filed Aug. 14, 2017, which claims priority to German Patent Application No. 10 2016 010 222.5, filed Aug. 20, 2016.

The invention relates to an apparatus for supplying dialysate, comprising a balancing device, which comprises at least one balancing chamber for balancing fresh and used dialysate, and a metering device for filling the at least one balancing chamber with permeate and concentrates in a specified mixing ratio for producing dialysate. The invention also relates to a dialysis apparatus comprising an apparatus for supplying dialysate and to a method for supplying dialysate for a dialysis apparatus.

In the event of chronic kidney failure, various methods for apparatus-based blood purification or blood treatment are used to remove substances which are normally excreted in urine and to remove fluid. Owing to the high volumes exchanged, fresh dialysate and used dialysate has to be precisely balanced, taking into account the volume of fluid removed from the patient via the membrane of the dialyser. The balancing precision has to meet very stringent requirements.

Balancing systems having balancing chambers that are divided into two balancing chamber halves by means of a flexible membrane can be found in the prior art. DE-A-28 38 414 C2 describes a dialysis apparatus comprising a balancing system having two balancing chambers which are each divided into two balancing chamber halves by means of a membrane, which halves are alternately operated in successive balancing chamber cycles of successive working cycles, and therefore one balancing chamber half is filled with fresh dialysate whilst used dialysate is removed from the other chamber half.

Prefabricated dialysate concentrates diluted with a specified volume of water are generally used to produce dialysate. Acidic and basic concentrates are used as the concentrates.

The water and the concentrates are mixed in what is referred to as a mixer circuit of the dialysis apparatus, which circuit comprises the balancing system. In the mixer circuit, the concentrates are added to the permeate (pure water) in a precisely specified volumetric ratio, the volumes being derived directly from the concentrates used and the specification of the dialysate to be produced. Known mixer circuits have a metering pump for every concentrate, which pumps simultaneously supply the balancing chambers with the respective concentrates within the individual balancing chamber cycles. In this case, supplying the concentrates within one balancing chamber cycle is a technical requirement. In practice, the fill time of a balancing chamber having a volume of 30 ml at a permeate flow rate of 1400 ml/min is just 1.3 seconds.

The object of the invention is to provide an apparatus for supplying dialysate for a dialysis apparatus, which makes it possible to precisely meter permeate and concentrates. Another object of the invention is to provide a dialysis apparatus in which the dialysate is produced in an exact mixing ratio of permeate to concentrates. Another object of the invention is to provide a method for supplying dialysate, in which the dialysate is mixed in a precisely specified volumetric ratio of permeate to concentrates. In particular, the object of the invention is to make the design less complex and reduce the costs of producing the dialysate.

These objects are achieved according to the invention by means of the features of the independent claims. The dependent claims relate to advantageous embodiments of the invention.

The apparatus according to the invention for supplying dialysate and the dialysis apparatus according to the invention comprising the apparatus for supplying dialysate are characterised by a simplified design and low production costs. Effort with regard to maintenance of the apparatus is also reduced. Another advantage is the compact construction and the reduced weight.

The apparatus for supplying dialysate has a balancing device which comprises at least one balancing chamber for balancing fresh and used dialysate, and a metering device for filling the at least one balancing chamber with permeate and concentrates in a specified mixing ratio for producing dialysate.

The metering device is designed such that specified volumes of concentrates are conveyed into the at least one balancing chamber in successive working cycles. Given that the specified volumes of concentrates are not added simultaneously, the concentrates can be conveyed using just one single metering pump. As a result, it is not necessary to have a plurality of metering pumps. This is advantageous in that the metering pump is a relatively expensive component of the mixer circuit. When there is just one metering pump, additional components are also dispensed with that would be necessary in the case of additional metering pumps. In practice, the design is simpler and compact and the maintenance costs are reduced.

A preferred embodiment of the metering device provides a metering pump, which has an inlet and an outlet, and a distributor assembly which comprises inlets for supplying the concentrates and an outlet. The outlet of the distributor assembly is connected to the inlet of the metering pump. Fluid lines for taking in the concentrates from concentrate sources can be connected to the inlets of the distributor assembly. The concentrate sources may be containers, for example canister or bags, in which the concentrate, for example an acidic concentrate and a basic concentrate, in particular bicarbonate, is provided.

The metering pump is preferably a membrane pump, in particular an eccentric membrane pump. The membrane pump allows precise and quick metering within the relatively short balancing chamber cycle. However, other pumps having sufficiently high metering precision and a sufficiently high delivery rate may also be used to meter the concentrate. If the delivery rate of the metering pump used is not sufficient, it is also possible to ensure that the balancing chamber is completely filled by limiting the maximum dialysate flow.

In another preferred embodiment, the distributor assembly comprises valves for opening and closing the inlets. The valves are controlled by a control unit which is configured such that the valves are not opened simultaneously, but rather one after the other for a specified time period in each case. The duration of the specified time periods has to be shorter than the time period of a balancing chamber cycle such that all of the concentrates can be added within one balancing chamber cycle.

In a particularly preferred embodiment, the balancing device comprises a first and a second balancing chamber, each of which is divided into a first and a second balancing chamber half by means of a membrane, and therefore, when one chamber half is filled with fresh dialysate, used dialysate is moved out of the other chamber half, or, when one chamber half is filled with used dialysate, fresh dialysate is moved out of the other chamber half. Fresh dialysate is supplied to the balancing device via a supply line and used dialysate is removed from the balancing device via a removal line. The balancing device is designed such that, in order to balance fresh and used dialysate, the balancing chamber halves are alternately filled and emptied in successive balancing chamber cycles of successive working cycles. Balancing chamber systems of this type can be found in the prior art.

The fresh dialysate is preferably produced by supplying permeate and concentrate to a mixing point. The mixing point may be upstream of the balancing chamber, and therefore the dialysate produced from permeate and concentrate flows into the balancing chamber, where permeate and concentrates can be mixed even further.

In another particularly preferred embodiment, the supply line of the balancing device for fresh dialysate leads away from a mixing point, to which run both a permeate conveying line for conveying permeate from a permeate source, and a concentrate conveying line which leads away from the outlet of the metering device.

The metering device may provide a rinsing mode for the metering pump that conveys various concentrates one after the other, in order to prevent concentrate residues in the metering pump from being able to react with one another. The metering pump is preferably rinsed using a rinsing fluid which is supplied to the inlet of the metering pump via a rinsing line. A valve may be provided in the supply line in order to interrupt the rinsing cycle, which valve can be controlled by means of the control unit. The control unit is preferably configured such that, between individual working cycles, in which a specified volume of a concentrate is conveyed into the at least one balancing chamber, the valve arranged in the rinsing line is open and the valves for opening and closing the inlets of the distributor assembly are closed.

The dialysis apparatus according to the invention has an extracorporeal blood circuit and a dialysate system which is separated from the extracorporeal blood circuit by means of a semi-permeable membrane of a filter or a dialyser, which dialyser comprises a blood chamber and a dialysate chamber, the blood chamber being part of the extracorporeal blood circuit and the dialysate chamber being part of the dialysate system. In the dialysis apparatus according to the invention, the apparatus for supplying dialysate is a component of the dialysate system of the dialysis apparatus. Therefore, the apparatus for supplying dialysate can also make use of components of the dialysis apparatus. For example, the control unit of the apparatus for supplying dialysate can be a component part of the central control and arithmetic unit of the dialysis apparatus.

In the following, an embodiment of the invention is described in greater detail with reference to the drawings, in which:

FIG. 1 is a simplified schematic view of a dialysis apparatus having an apparatus for supplying dialysate. FIG. 1 only shows the components of the dialysis apparatus that are essential to the invention.

Figure 1:
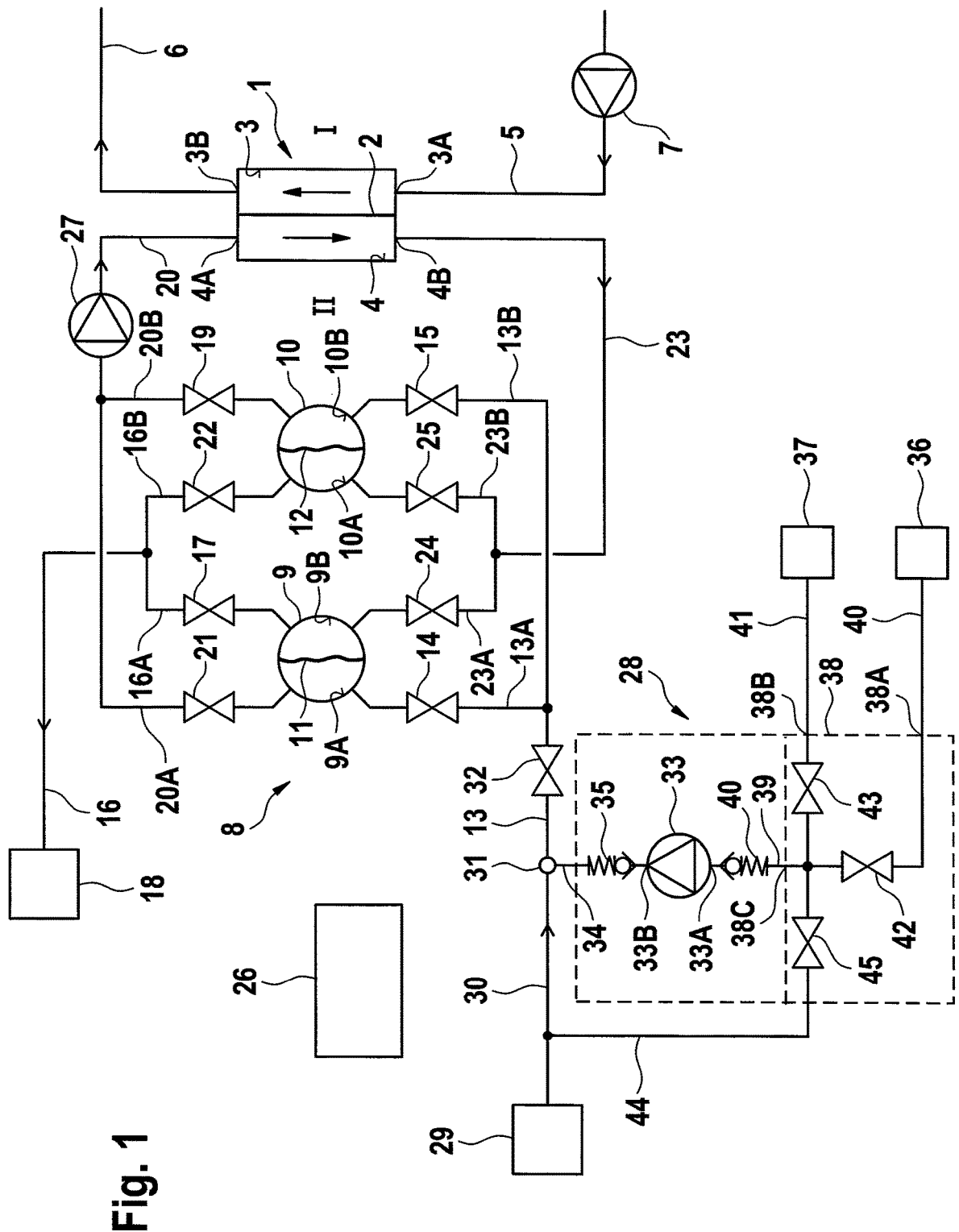
FIG. 1 is a simplified schematic view of the essential components of the dialysis apparatus according to the invention comprising the apparatus according to the invention for supplying dialysate.

The dialysis apparatus comprises a dialyser 1 which is divided into a blood chamber 3 and a dialysate chamber 4 by means of a semi-permeable membrane 2. A blood supply line 5 is connected to the inlet 3A of the blood chamber 3 and a blood removal line 6 is connected to the outlet 3B of the blood chamber 3. The patient's blood is conveyed in the extracorporeal blood circuit I by means of a blood pump 7 provided in the blood supply line 5.

The fluid system II comprises a balancing device 8 which is described in detail in DE 28 38 414 C2 and to which reference is explicitly made.

The balancing device 8 comprises a first balancing chamber 9 and a second balancing chamber 10. The balancing chambers 9, 10 each comprise a rigid housing which is divided into a first and a second balancing chamber half 9A, 9B and 10A, 10B, respectively, by means of a flexible membrane 11, 12.

A first portion 13A of a supply line 13 for fresh dialysate runs to an inlet of the first balancing chamber half 9A of the first balancing chamber 9, in which first portion a first valve 14 is arranged, and a second portion 13B of the supply line 13 for fresh dialysate runs to an inlet of the second balancing chamber half 10B of the second balancing chamber 10, in which second portion a second valve 15 is arranged. A first portion 16A of a removal line 16 for used dialysate runs from an outlet of the second balancing chamber half 9B of the first balancing chamber 9 to a discharge 18, in which first portion a third valve 17 is arranged. A second portion 16B of the removal line 16 for used dialysate runs from an outlet of the first balancing chamber half 10A of the second balancing chamber 10 to the discharge 18, in which second portion a fourth valve 19 is arranged.

An outlet of the first balancing chamber half 9A of the first balancing chamber 9 and an outlet of the second balancing chamber half 10B of the second balancing chamber 10 are connected to an inlet of the dialysate chamber 4A of the dialyser 1 by means of a first and second portion 20A, 20B, respectively, of a supply line 20 for fresh dialysate, a fifth and a sixth valve 21, 19 being arranged in the first and second portions, respectively, of the supply line. An outlet of the dialysate chamber 4 of the dialyser 1 is connected to an inlet of the second balancing chamber half 9B of the first balancing chamber 9 and to an inlet of the first balancing chamber half 10A of the second balancing chamber 10 by means of a removal line 23 for used dialysate. A seventh and an eighth valve 24, 25 are arranged in the associated line portions 23A, 23B of the removal line 23. The valves can be electromagnetically or pneumatically actuatable valves.

A dialysate pump 27 is arranged in the supply line 13 in order to convey the dialysate into the dialysate chamber 4 of the dialyser 1.

The valves are controlled by means of a control unit 26 which is connected to the valves via control lines (not shown), and therefore the valves can be actuated. The control unit 26 also controls the blood pump 7 and the dialysate pump 27 to set the flow rates of the pumps.

The control unit may comprise a general processor, a digital signal processor (DSP) for continuously processing digital signals, a microprocessor, an application-specific integrated circuit (ASIC), an integrated circuit consisting of logic elements (FPGA), or other integrated circuits (IC) or hardware components in order to carry out the individual method steps. A data-processing program (software) can run on the hardware components in order to carry out the method steps. A plurality or combination of the various components is also possible.

The valves form two groups of valves, the first, third, sixth and eighth valves 14, 17, 19, 25 forming a first group and the second, fourth, fifth and seventh valves 15, 22, 21, 24 forming a second group.

The control unit 26 is configured such that the valves 14, 17, 19, 25 of the first group are open when the valves 15, 22, 21, 24 of the second group are closed, and vice versa. As a result, the two balancing chambers 9, 10 operate alternately, the balancing chamber halves 9A, 9B and 10A, 10B being alternately filled and emptied, respectively, in successive balancing chamber cycles. The chambers are filled and emptied in individual balancing chamber cycles of one working cycle of successive working cycles.

If, for example, the valves 14, 17, 19, 25 of the first group are open, fresh dialysate is conveyed into the first balancing chamber half 9A of the first balancing chamber 9, whereas used dialysate flows out of the second balancing chamber half 9B of the first balancing chamber 9 and into the discharge 18. Fresh dialysate flows out of the second balancing chamber half 10B of the second balancing chamber 10 and into the dialysate chamber 4 of the dialyser 1 and used dialysate flows into the first balancing chamber half 10A of the second balancing chamber 10.

The apparatus according to the invention for supplying dialysate for the dialyser of the dialysis apparatus comprises the balancing device 8 and a metering device 28 for filling the balancing chambers 9, 10 of the balancing device 8 with permeate and concentrates in a specified mixing ratio.

The permeate (water) is provided in a permeate source 29. A permeate conveying line 30 runs from the permeate source 29 to a mixing point 31, from which the supply line 13 for fresh dialysate of the balancing device 8 leads to the balancing chambers 9, 10, and therefore permeate can flow into the balancing chambers of the balancing device. A valve 32 is arranged in the supply line so as to interrupt the supply of dialysate.

The metering device 28 has a metering pump 33, in particular a membrane pump, which comprises an inlet 33A (intake side) and an outlet 33B (delivery side). The outlet 33B of the membrane pump is connected to the mixing point 31 via a concentrate conveying line 34, in which a check valve 35 can be arranged. In the present embodiment, a specified volume of a first concentrate, for example an acidic concentrate, and a specified volume of a second concentrate, for example a basic concentrate, in particular bicarbonate, is added, by means of the metering pump 33, to the permeate at the mixing point 31. The first and second concentrates are provided in containers 36, 37.

Furthermore, the metering device 28 comprises a distributor assembly 38 which comprises a first inlet 38A for supplying the first concentrate and a second inlet 38B for supplying the second concentrate, and an outlet 38C. The outlet 38C of the distributor assembly 38 is connected to the inlet 33A of the metering pump 33 via a fluid line 39, in which a check valve 40 can be arranged. A first intake line 40 is connected to the first inlet 38A and runs to the first container 36, and a second intake line 41 is connected to the second inlet 38B and runs to the second container 37. A valve 42, 43, for example an electromagnetically actuatable valve, is provided to open and close the first and second inlet, respectively.

The dialysate system may also comprise a degassing circuit; this, however, not being shown in FIG. 1.

In the present embodiment, the line portion of the permeate conveying line 30, upstream of the mixing point 31, is connected to the inlet 33A (intake side) of the metering pump 33 via a rinsing line 44, in which an additional valve 45 is arranged.

The control unit 26 of the balancing device 8 also controls the valves 42, 43 of the distributor assembly 28 and the valves 32, 45 in the supply line 13 and the rinsing line 44. The control unit 26 is configured such that the two concentrates are added one after the other at the mixing point 31 in one balancing chamber cycle during the filling phase.

If, for example, the valves 14, 17, 19, 25 of the first group are open in one balancing chamber cycle during the filling phase so as to convey dialysate into the first balancing chamber half 9A of the first balancing chamber 9, the first valve 42 of the distributor assembly 38 is opened for a specified first time period, the metering pump 33 taking in the first concentrate from the first concentrate container 36 and adding said first concentrate to the mixing point 31 within the specified first time period. If the first valve 42 is closed again, the second valve 43 of the distributor assembly 38 is opened for a specified second time period, the metering pump 33 taking in the second concentrate from the second concentrate container and adding said second concentrate to the mixing point within the specified second time period. The first and second time periods have to be shorter than the duration of the balancing chamber cycle during the filling phase, so that the concentrates can be added during the filling phase. It is possible to ensure that the relevant balancing chamber is filled completely by monitoring the filling pressure, for example. The duration of the first and second time periods determines the volumetric ratio of permeate to concentrate and is specified by the control unit 26 on the basis of the desired composition of the dialysate. The metering pump 33 is therefore operated in one balancing chamber cycle of the balancing device in successive working cycles.

To prevent concentrate residue of the first concentrate from reacting with concentrate residue of the second concentrate in the metering pump 33, the metering pump can be rinsed between the first and second working cycles in each of which a concentrate is added. During the rinsing phase, the valve 32 in the supply line 13 is closed and the valve 45 in the rinsing line 44 is open, and the first and second valves 42, 43 of the distributor assembly 38 are closed, the metering pump 33 being operated such that permeate circulates in a rinsing circuit.

Figure 2:
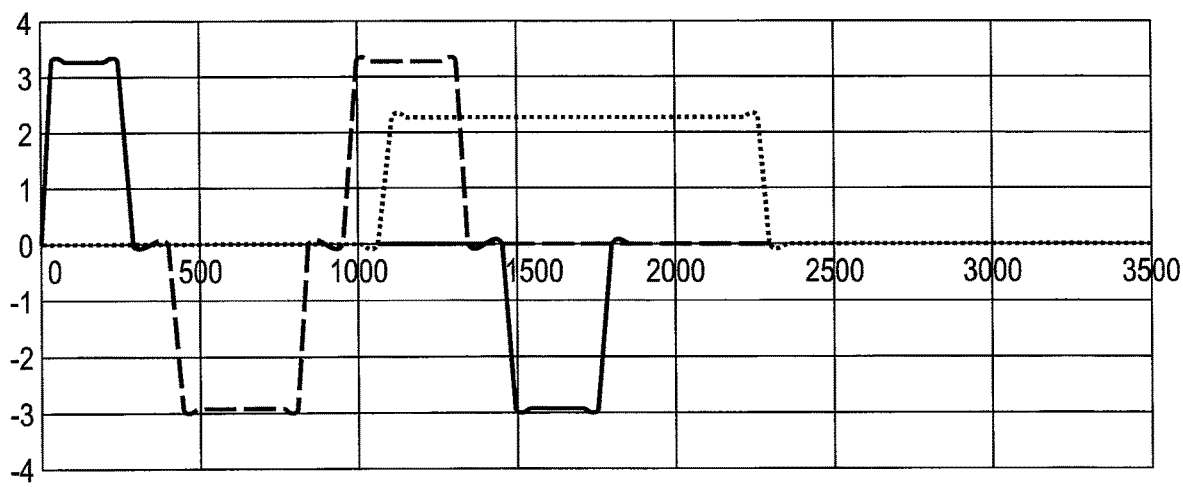
FIG. 2 shows the flow of the concentrates during a balancing chamber cycle of the balancing device when there is no rinsing phase.

FIG. 2 shows the flow of the first and second concentrate during a balancing chamber cycle of the balancing device 8 for filling a balancing chamber, when there is no rinsing phase. In the present embodiment, the balancing chamber has a volume of 30 ml. In the embodiment, the metering volume of the first concentrate is 8284 and the metering volume of the second concentrate is 1159 μL. In FIG. 2, the x axis represents the time in milliseconds (ms), and the y axis represents the flow of the metering pump [μL/s]/filling flow of the balancing chamber [ml/min]/10. A negative flow means that the metering pump 33 is taking in concentrate. The concentrate flow of the first concentrate is indicated by a solid line and the concentrate flow of the second concentrate is indicated by a dashed line. A dotted line indicates the balancing chamber being filled with permeate (pure water) from a degassing circuit. The figure shows that the concentrates are added, in sequence, within the duration of the balancing chamber cycle.

Figure 3:
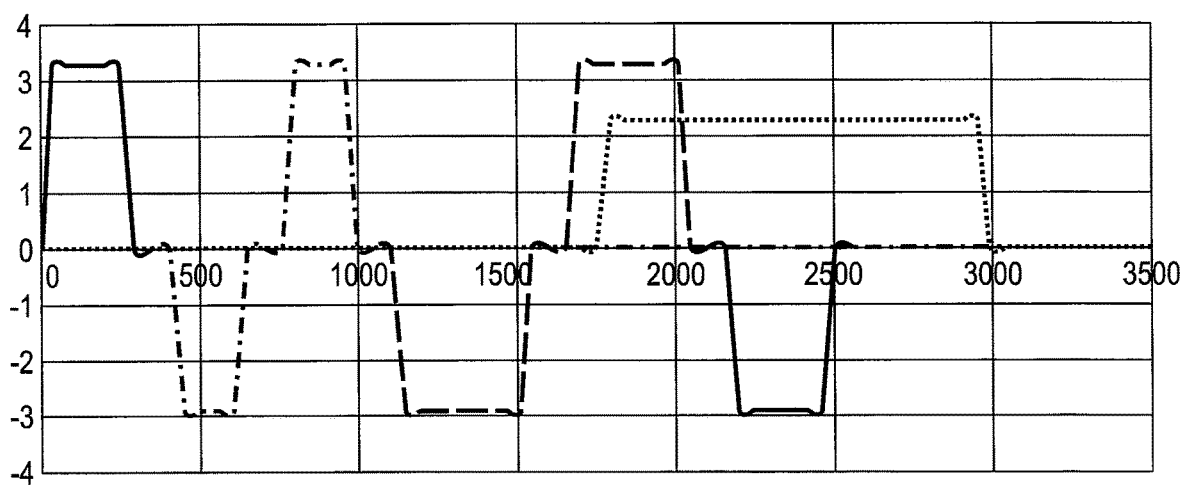
FIG. 3 shows the flow of the concentrates during a balancing chamber cycle of the balancing device when there is a rinsing phase.

FIG. 3 shows the flow of the first and second concentrate during a balancing chamber cycle of the balancing device 8 for filling a balancing chamber, when there is a rinsing phase. In FIG. 3, the flow of the rinsing fluid (permeate) is indicated by a dot-and-dash line. Rinsing is carried out in a time period between adding the first concentrate and adding the second concentrate. In the embodiment, the rinsing volume is 580 μL. Rinsing lengthens the time taken to serially add the concentrates. The figure shows, however, that all the concentrate is added within one balancing chamber cycle.

The invention claimed is:

1. An apparatus for supplying dialysate for a dialysis apparatus, comprising
    a balancing device that comprises at least one balancing chamber for balancing fresh and used dialysate, and
    a metering device for filling the at least one balancing chamber with permeate and concentrates in a specified mixing ratio for producing dialysate,
    wherein
    the metering device comprises a single metering pump and a distributor assembly, the metering device is designed such that specified volumes of the concentrates are conveyed from the distributor assembly into the at least one balancing chamber, in successive working cycles, using the single metering pump.

2. An apparatus for supplying dialysate for a dialysis apparatus, comprising
    a balancing device that comprises at least one balancing chamber for balancing fresh and used dialysate, and
    a metering device for filling the at least one balancing chamber with permeate and concentrates in a specified mixing ratio for producing dialysate,
    wherein
    the metering device is designed such that specified volumes of the concentrates are conveyed into the at least one balancing chamber in successive working cycles, the metering device comprises a metering pump that has an inlet and an outlet, the metering device comprises a distributor assembly that comprises inlets for supplying the concentrates from concentrate sources, and the distributor assembly comprises an outlet that is connected to the inlet of the metering pump.

3. The apparatus according to claim 2, characterised in that the distributor assembly comprises valves for opening and closing the inlets, the metering device comprising a control unit for the valves that is configured such that the valves are opened one after the other for a specified time period in each case.

4. The apparatus according to claim 2, characterised in that the metering pump is a membrane pump.

5. The apparatus according to claim 3, characterised in that the balancing device comprises:
    a first and a second balancing chamber, each of which is divided into a first and a second balancing chamber half by means of a membrane, and therefore, when one chamber half is filled with fresh dialysate, used dialysate is moved out of the other chamber half, or, when one chamber half is filled with used dialysate, fresh dialysate is moved out of the other chamber half, and
    a line for supplying fresh dialysate to the balancing device and a line for removing used dialysate from the balancing device,
    the balancing device being designed such that, in order to balance fresh and used dialysate, the balancing chamber halves are alternately filled and emptied in successive balancing chamber cycles of successive working cycles.

6. The apparatus according to claim 5, characterised in that the control unit is configured such that the valves are opened one after the other in a balancing chamber cycle for a specified time period in each case.

7. The apparatus according to claim 5, characterised in that the supply line for fresh dialysate leads away from a mixing point, to which run both a permeate conveying line for conveying permeate from a permeate source, and a concentrate conveying line which leads away from the outlet of the metering pump.

8. The apparatus according to claim 3, characterised in that a rinsing line for supplying a rinsing fluid runs to the inlet of the metering pump, in which rinsing line a valve is arranged.

9. The apparatus according to claim 8, characterised in that the control unit is configured such that, between individual working cycles, in which a valve is open for a specified time period, the valve arranged in the rinsing line is open and the valves for opening and closing the inlets of the distributor assembly are closed.

10. A dialysis apparatus comprising an extracorporeal blood circuit and a dialysate system that is separated from the extracorporeal blood circuit by means of a semi-permeable membrane of a dialyser, which dialyser comprises a blood chamber and a dialysate chamber, wherein the blood chamber is part of the extracorporeal blood circuit and the dialysate chamber is part of the dialysate system, and the dialysate system comprises an apparatus for supplying dialysate according to claim 1.

11. A method for supplying dialysate for a dialysis apparatus that comprises a balancing device, a metering device, and a distributor assembly, the balancing device comprising at least one balancing chamber for balancing fresh and used dialysate, the at least one balancing chamber being filled with permeate and concentrates in a specified mixing ratio for producing dialysate, the metering device being configured for filling the at least one balancing chamber with permeate and concentrates in a specified mixing ratio for producing dialysate, the metering device comprises a metering pump that has an inlet and an outlet, the distributor assembly comprises inlets for supplying the concentrates from concentrate sources, and an outlet, and the outlet of the distributor assembly is connected to the inlet of the metering pump, wherein the method comprises conveying, by means of the metering pump, specified volumes of the concentrates into the at least one balancing chamber in successive working cycles.

12. The method according to claim 11, characterised in that, in order to balance fresh and used dialysate in successive balancing chamber cycles of successive working cycles, the balancing chamber halves of at least one balancing chamber are alternately filled and emptied, and in that, in one balancing chamber cycle, specified volumes of the concentrates are conveyed into the at least one balancing chamber in successive working cycles.

13. The method according to claim 11, characterised in that the metering pump is rinsed with a rinsing fluid during a rinsing cycle between individual working cycles, in which a specified volume of a concentrate is conveyed into the at least one balancing chamber.

14. The method according to claim 13, characterised in that the rinsing fluid is permeate.

\* \* \* \* \*